United States Patent [19]

Hoftman

[11] Patent Number: 5,729,879
[45] Date of Patent: Mar. 24, 1998

[54] SURGICAL BLADE REMOVAL AND DISPOSAL DEVICE

[75] Inventor: Mike M. Hoftman, Canoga Park, Calif.

[73] Assignee: DeRoyal Industries, Inc., Powell, Tenn.

[21] Appl. No.: 352,988

[22] Filed: Dec. 9, 1994

Related U.S. Application Data

[63] Continuation of Ser. No. 849,477, Mar. 11, 1992, abandoned.

[51] Int. Cl.$^6$ .......................... B23P 19/04; B65D 83/00; B65D 25/00; B65F 7/00
[52] U.S. Cl. .................... 29/239; 29/278; 206/355; 206/359
[58] Field of Search .................... 29/239, 426.5, 29/426.6, 278; 206/355, 359

[56] References Cited

U.S. PATENT DOCUMENTS

| | | |
|---|---|---|
| 4,106,620 | 8/1978 | Brimmer et al. |
| 4,180,162 | 12/1979 | Magney |
| 4,270,416 | 6/1981 | Thompson |
| 5,088,173 | 2/1992 | Kromer et al. ............... 206/355 X |

Primary Examiner—Joseph M. Gorski
Attorney, Agent, or Firm—Loeb & Loeb

[57] ABSTRACT

A disposable case for deposing surgical blades includes a surgical blade removal device for removing a blade from a surgical knife handle. The case has an upper half and a bottom half connected by hinge means for allowing the upper half and the bottom half to be opened or closed, and also includes latches for securing the upper half and the bottom half together. Magnetic means are provided on the bottom half for retaining the blades thereon, with counting indicia provided thereon for designating and counting the blades that are to be disposed. A pad is provided on the outer surface of the upper half for receiving an adhesive tape, wherein the adhesive tape may be peeled from the pad and secured onto portions of the upper half and the bottom half to secure the case in a closed position. The blade removal device comprises a blade seat for receiving the blade, a handle seat for receiving the handle, a dividing wall provided between the blade seat and the handle seat and having a sharp curved edge for separating the blade from the handle, and a restraining wall for restraining the blade from rearward movement once the blade has been positioned in the blade seat and the handle withdrawn rearwardly.

8 Claims, 4 Drawing Sheets

SURGICAL BLADE REMOVAL AND DISPOSAL DEVICE

This application is a continuation of U.S. application Ser. No. 07/849,477, filed on Mar. 11, 1992, and now abandoned.

BACKGROUND OF THE INVENTION

1. Background of the Invention

The present invention relates in general to the removal of disposable surgical blades from surgical knife handles, and in particular, to a device for removing used disposable blades from surgical knife handles and for safely disposing of the removed blades.

2. Description of the Related Art

It is common practice during surgical operations for a surgeon to use one or more blades to perform the surgical procedure. During the course of surgery some of the disposable blades may get dull or become contaminated and must be replaced by new sharp, sterile blades. Also at the end of the surgical procedure the surgical staff must remove the contaminated blades and safely dispose of them.

A conventional surgical knife handle is shown at 10 in FIG. 1 and has a handle portion 12 and a narrow inserted portion 14 connected by a neck portion 16. The inserted portion 14 is located at the forward end of the handle 10 and is adapted to hold a blade 18. The inserted portion 14 has a rounded front end 20 and a rounded rear end 22 with grooves 24 provided around the outer periphery. The blade 18 has a keyed slot 26 with a narrow portion 28 and a wider portion 30 located towards the rear of the slot 26. In operation, the front end 20 of the inserted portion 14 is inserted into the wider portion 30 of the slot 26 and the narrow portion 28 of the slot 26 slides in the grooves 24 until the rear of the slot 26 clears the rear end 22 of the inserted portion 14, at which point the blade 18 is fitted in place on the inserted portion 14. When the blade 18 is in its normal position on the inserted portion 14 of the handle 10, the rear end 22 of the inserted portion 14 engages a rear edge 32 of the blade slot 26, which prevents the blade 18 from moving along its slot 26 along the grooves 24 of the inserted portion 14. Additionally, the rear edge 34 of the blade 18 may abut a surface 36 of the handle 10 to help prevent movement of the blade 18.

In the past, in order to remove a blade 18 from the conventional surgical knife handle 10, a nurse will typically use a surgical tool or his or her fingers to disengage the rear edge 32 of the slot 26 of the blade 18 from the rear end 22 of the inserted portion 14 of the handle 10, and then begin sliding the blade slot 26 along the inserted portion 14. This results in an uncontrolled bending of the blade 18 within its elastic limit so that when the inserted portion 14 reaches the wider portion 30 of the slot 26, the blade 18 has a tendency to snap upward. Such bending and sliding of the blade is dangerous because it may cut the nurse. The blade may also be propelled away from the operating area where someone would have to retrieve. The blade may then be lost temporarily. Furthermore, while removing a blade 18 from a handle 10, the nurse's hand may be cut if his or her hand accidentally slips along the blade 18.

Thus, there is a need to facilitate the safe removal and disposal of blades from surgical knife handles. One such attempt to address this problem is the surgical blade removal and disposal device disclosed in U.S. Pat. No. 4,318,473 to Sandel, issued Mar. 9, 1982. This patent discloses the use of a blade removing portion which has a guide integral with a case for guiding the handle and its associated blade therethrough. The guide includes a slot deeper than the handle for receiving the handle and for permitting the handle to move downward. The guide also includes a shoulder positionable under the blade for supporting the rear of the blade. When the handle moves downward in the slot, the inserted portion pulls the central portion of the blade down causing it to bow on the shoulder and the forward portion of the case releasing the rear edge of the blade between the blade slot and the handle and permitting the slot of the handle to slide on the inserted portion. The guide also has a stop integral with the case rearward of the shoulder and above the top of the blade prior to bowing the blade for engaging the rear of the blade. The stop also functions to prevent rearward motion of the blade when it is bowed so that the inserted portion moves in the slot to a wider portion of the slot thereby disengaging the blade from the handle. An abutment forward of the guide and integral with the case positioned over the forward portion of the blade and a guard over the rear of the blade prevent the forward and rear portions of the blade from snapping off the case when the blade is disengaged from the inserted portion.

However, this surgical blade removal and disposal device suffers from a number of drawbacks. First, in order to facilitate safe and proper removal of blades, the blade must be placed at a proper angle in the guide means to allow the blade removal operation to take place. Second, the blade must be aligned appropriately within the guide means. Third, although a larger blade may be removed by this surgical blade removal and disposal device, the removal of such large blades requires bending and twisting of the handle and the blade, which is both dangerous and difficult.

In addition to the safe removal and disposal of surgical blades, the surgical staff must maintain strict accountability for all surgical sharps and/or instruments to ensure that none remain in the patient after surgery, or that none of the surgical sharps and/or instruments are lost or lying around the operating room which may cause injury to the unwary. After removal of a blade, it is placed in a disposal unit so that an accounting can be made of the disposed blades and other sharp objects which when added to the unused blades must equal the number of all blades brought into the surgery.

SUMMARY OF THE DISCLOSURE

In order to accomplish the objects of the present invention, a disposable case according to embodiments of the present invention includes a surgical blade removal and disposal device for removing a blade from a surgical knife handle. The handle has a narrow inserted portion provided at a front end thereof and grooves provided along the periphery of the inserted portion, while the blade has a slot for receiving the inserted portion, the grooves being slidable in the slot and passing through a wider opening at a portion of the slot to permit the blade to be removed from the inserted portion.

The case according to embodiments of the present invention has an upper half and a bottom half connected by hinge means for allowing the upper half and the bottom half to be opened or closed, and also includes latches for securing the upper half and the bottom half together. Magnetic or other means are provided on the bottom half for retaining the blades and other sharps thereon, with counting indicia provided thereon for designating and counting the blades and other sharps that are to be disposed. A pad is provided on the outer surface of the upper half for receiving an adhesive tape, wherein the adhesive tape may be peeled from the pad and secured onto portions of the upper half and the lower half to secure the case in a closed position.

The blade removal device according to embodiments of the present invention comprises a blade seat for receiving the blade, a handle seat for receiving the handle, a dividing wall provided between the blade seat and the handle seat and having a sharp curved edge for separating the blade from the handle, and a restraining wall for restraining the blade from rearward movement once the blade has been positioned in the blade seat. The handle may be urged rearwardly to cause the blade slot to slide along the grooves of the inserted portion while the rear edge of the blade is restrained from rearward movement by the restraining wall.

The present invention discloses a surgical blade removal device which allows the blade to be removed from a surgical knife handle safely and without physically touching the blade. This surgical blade removal device is simple to operate so that blades can be easily removed from surgical knife handles in a safe and simple operation. This surgical blade removal device is incorporated into a disposal case which also provides for easy storage and accountability of the blades and other sharp objects used in surgery. This disposable case is a unitary, low cost plastic case which sits flat on any surface. Once all the blades have been accounted for, this disposable case has means provided to easily and effectively seal the case so that the case does not open and expose the blades and/or other sharp objects such as hypodermic needles or suture needles to the environment, thereby allowing for the easy and safe disposal of used blades and other sharp objects.

BRIEF DESCRIPTION OF THE DRAWINGS

Further objects, advantages and features of the invention will become apparent from the detailed description of the preferred embodiments when read in conjunction with the accompanying drawings, in which.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating general principles of embodiments of the invention. The scope of the invention is best defined by the appended claims.

Figure 2:
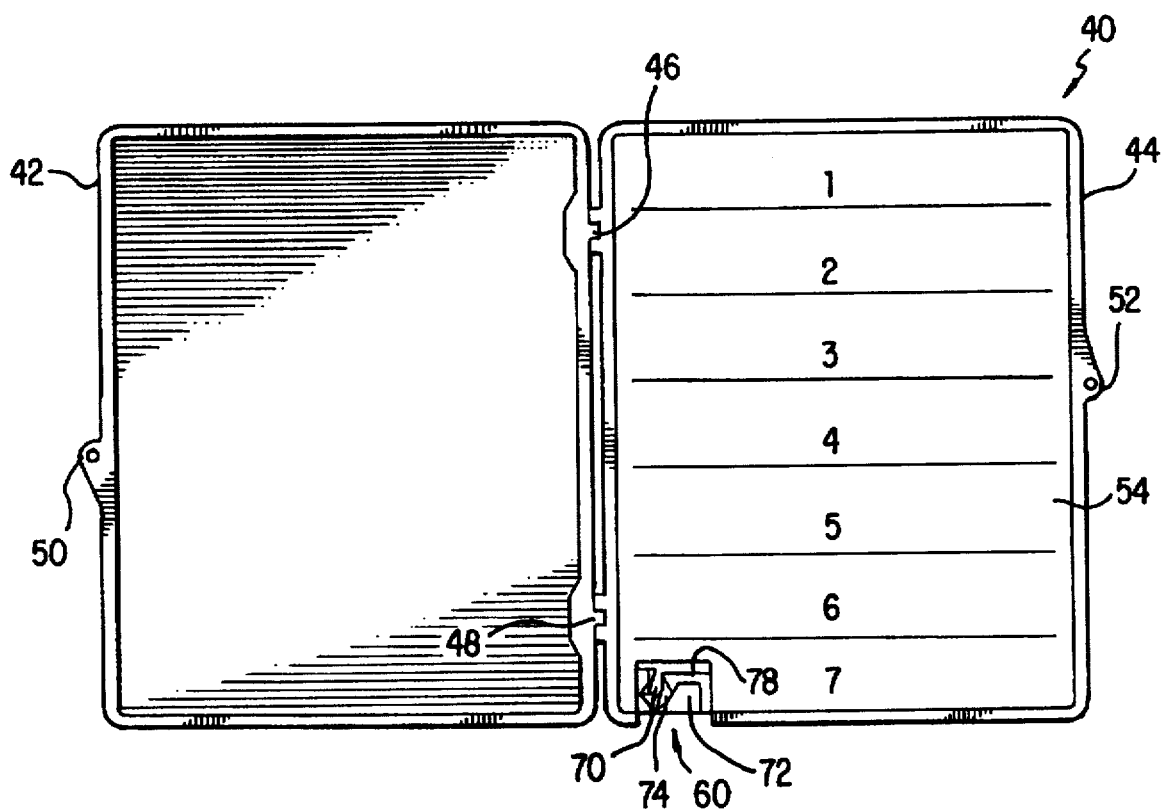
FIG. 2 is a top plan view of a disposable case incorporating the surgical blade removal and disposal device of the present invention therein.
Figure 2A:
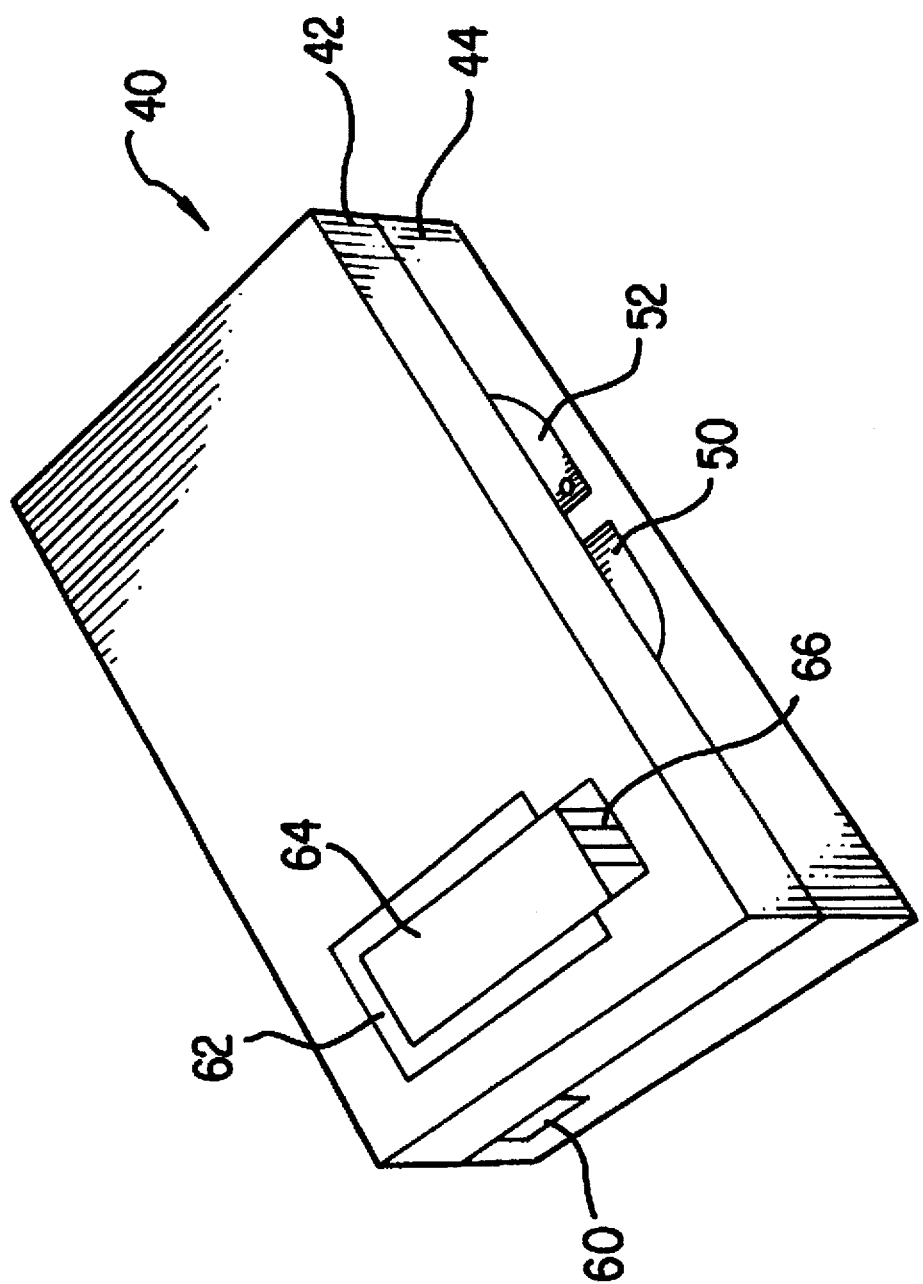
FIG. 2A is a perspective view of the disposable case of FIG. 2 in a closed position.

A detailed description of the preferred exemplary embodiment of the disposable case and the blade removal device according to the present invention will be made with reference to FIGS. 2–5. Referring to FIGS. 2 and 2A, the disposable case 40 is made of a molded plastic material and is comprised of a top half 42 and a bottom half 44 which are hinged in a conventional manner by hinges 46 and 48 so that the top half 42 and the bottom half 44 may be provided in the opened position of FIG. 2, or in a closed position of FIG. 2A. A pair of conventional integrally molded latches 50 and 52 are provided to facilitate the closure and locking of the case 40 for the disposal of any blades contained therein. It will be appreciated by those skilled in the art that many alternative forms of latching the case 40 may be used without departing from the spirit and scope of the present invention.

In the exemplary embodiment, the top half 42 is made of a transparent material while the bottom half 44 is provided with a large magnetic surface 54 covering the entire base of the bottom half 44 in a manner as taught in U.S. Pat. No. 4,013,109 to Sandel, issued Mar. 22, 1977, and incorporated herein by this reference. The magnetic surface 54 may be provided by a conventional rubber magnet material with counting indicia thereon to facilitate the counting and retention of blades and other sharp objects, i.e., suture needles and hypodermic needles. It will be appreciated by those skilled in the art that many alternative means for holding and counting sharp surgical objects may be used without departing from the spirit and scope of the present invention. Blade removal means are provided within the case 40 at a cut-out portion thereof as indicated generally at 60, and explained in detail hereinbelow.

Referring to FIG. 2A, the outer surface of the upper half 42 of the case 40 is provided with a liner 62 on which a piece of adhesive tape 64 is applied. The adhesive tape 64 has a thin strip 66 which acts as a handle and which does not have any adhesive applied thereon. In operation, after the case 40 is closed and latched, a nurse may grip the strip 66 and pull the adhesive tape 64 off the liner 62, then wrap the adhesive tape 64 around the upper half 42 and the bottom half 44 to secure the case 40 in a closed position. It will be appreciated by those skilled in the art that the adhesive tape 64 can be made from any conventional adhesive or securing tape. The reason for this security tape 64 is that the latches 50 and 52 may fail. This is especially true due to molding factors and through use, latches 50 and 52 can become looser and looser. This allows case 40 to open following disposal to a "red" bag in the operating room, releasing hypodermic needles and other sharp objects outside the case 40. This can then put the housekeeping personnel or others at risk of being stuck by a contaminated needle as they pick up the bags for disposal. In today's concerns of Aids and hepatitis and other infectious diseases, it is important to secure all the sharp objects in a secured, rigid container to ultimate disposal.

Figure 3:
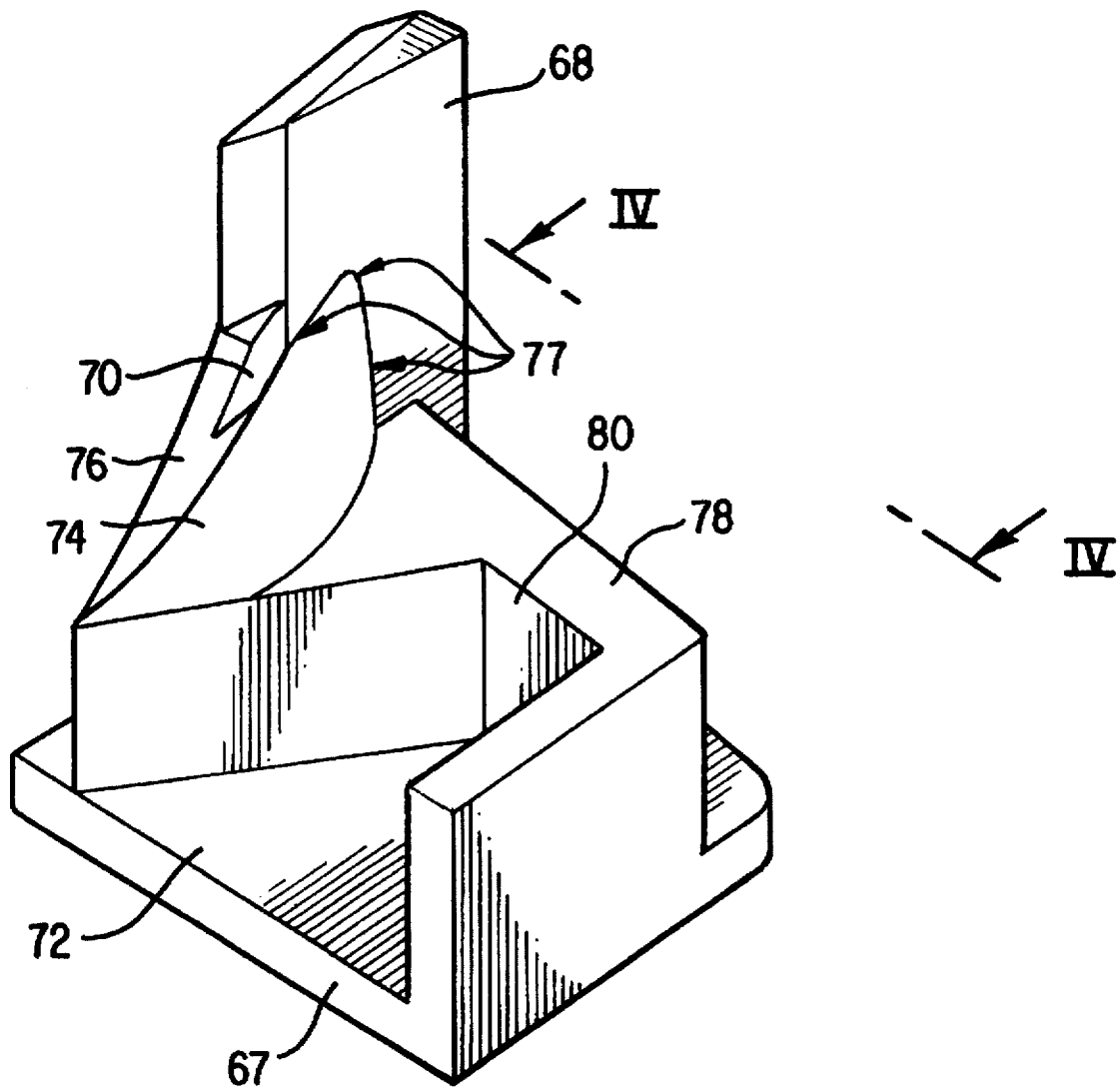
FIG. 3 is a perspective view of the surgical blade removal and disposal device of FIG. 1.
Figure 4:
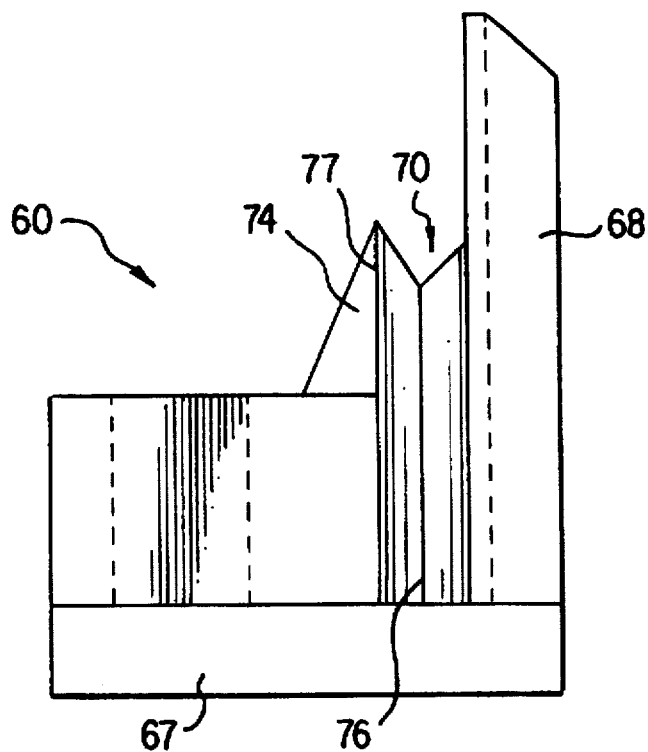
FIG. 4 is a rear view looking through plain IV—IV of FIG. 3 showing the blade removal and disposal device.
Figure 5:
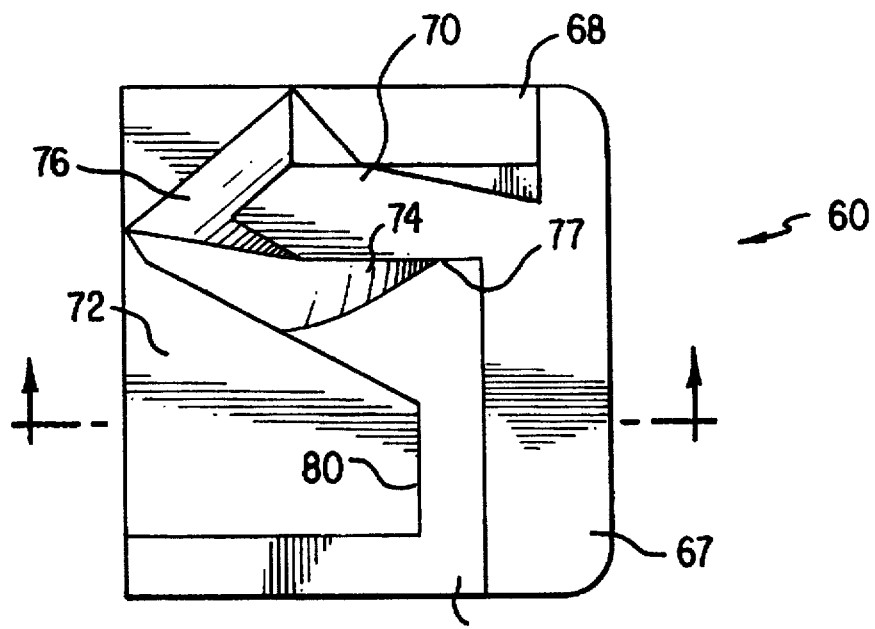
FIG. 5 is a top plan view of the blade removal and disposal device of FIG. 3.

Referring to FIGS. 3–5, the blade removal device 60 is carved and molded from rigid plastic material or a metal fabricated one and is seated upon a base 67. The blade removal device 60 is carved so that it comprises a guiding wall 68, a blade seat 70 and a handle seat 72. The blade seat 70 is V-shaped and is defined on one side by the guiding wall 68 and on the other side by a curved dividing wedge-shaped wall 74, with a V-shaped restraining wall 76 provided therebetween. The dividing wedge-shaped wall 74 acts to separate the blade seat 70 from the handle seat 72, and has a sharp curved edge 77. The handle seat 72 is defined by a N-shaped portion 78, with its left leg portion molded integrally with the dividing wedge-shaped wall 74.

Figure 1:
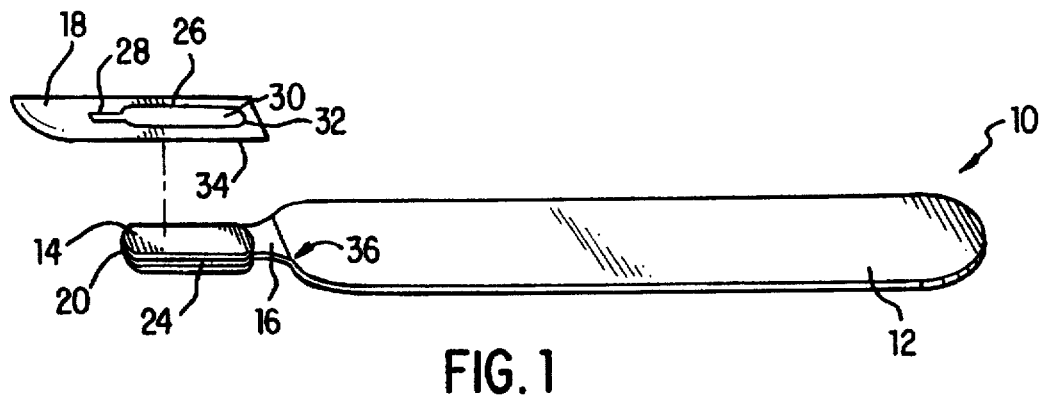
FIG. 1 is a perspective view of a conventional surgical knife handle and a conventional blade which may be used with the present invention.

The operation of the blade removal device 60 is described in connection with a conventional blade and handle as shown in FIG. 1, although it is appreciated by those skilled in the art that it may be used in connection with any conventional blade and handle. In operation, the blade 18 attached to the handle 10 is slid so that the blade 18 slides along the space between the pillar 68 and the dividing wedge-shaped wall 74, while the handle 10 occupies the handle seat 72 until the rear surface 36 of the handle 10 abuts an inner wall 80 of the N-shaped portion 78. In this position, the handle portion 12 of the handle 10 rests in the handle seat 72 while the entire length of the blade 18 lies within the blade seat 70 in the case 40 with the rear edge 34 of the blade 18 between the guiding wall 68 and the dividing wedge-shaped wall 74. At this position the rear edge 34 of the blade 18 is separated from the neck portion 16 by a force exerted by the dividing wedge-shaped wall 74 such that the rear edge clears the rear end 22 of the inserted portion 14. The handle blade combination is used in a very natural and the same way and position as it is used in surgery—in an upright position with the sharp part of the blade facing down. At this point, the entire blade 18/handle 10 assembly is pressed downward in the blade removal device 60 with the blade 18 occupying the blade seat 70 and the front end of handle portion 12 occupying the handle seat 72. In this position, the sharp edges of the blade 18 are pointing downwardly at the magnetic surface 54, and the sharp curved edge 77 of the dividing wall 74 is fitted between the rear edge 34 of the blade 18 and the rear surface 36 of the neck portion 16 of the handle 10. This causes the rear of blade 18 to bow, and disengages the rear edge 34 of the blade 18 from the rear surface 36 of the handle 10 in a controlled and consistent manner. The handle 10 may then be pulled rearwardly away from the case 40 to cause the grooves 24 of the narrow portion 14 of the handle 10 to slide along the narrow portion 28 of the slot 26 until the narrow portion 28 of the slot 26 is completely disengaged from the grooves 24. The V-shaped restraining wall 76 restrains the blade 18 from moving rearwardly and allows the handle 10 to be cleanly disengaged from the blade 18.

Thus, the blade seat 70 provides a seat for securely holding the blade 18 while the handle 10 is being disengaged. Furthermore, the sharp curved edge 77 of the dividing wedge-shaped wall 74 is used to separate the rear edge 34 of the blade 18 from the rear surface 36 of the handle 10 to achieve the disengagement. After the handle 10 has been completely pulled out of the case 40, the blade 18, which was resting in the blade seat 70, falls into the bottom half 44 of the case 40.

Thereafter, the front end 20 of the handle 10 may be used to move the blade 18 to the desired location on the bottom half 44 of the case 40. The same procedure may be repeated to remove other used and/or contaminated surgical knife blades. After the entire case 40 has been filled with used blades and other sharp objects, the case 40 may be closed, the adhesive tape 64 applied to seal the top half 42 and the bottom half 44 together as well as the latches 50 and 52, and the case 44 together with its used blades and other sharp objects may be accounted for and disposed of in a safe, simple and efficient manner. If the case 40 needs to be reopened for recounting, the security tape 64 can be removed and rested in its original place over the liner 62 and replaced again following recounting.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for removing surgical blades from a surgical knife handle and for holding the removed blades, each blade having a rear edge which abuts a rear surface of a neck of the handle in a locking relationship, the handle further having a narrow inserted portion provided at a front end thereof and grooves provided along the periphery of the inserted portion, the blade also having a slot for receiving the grooves of the inserted portion of the handle, the grooves being slidable in the slot and passing through a wider opening at a portion of the slot to permit the blade to be removed from the inserted portion, the device comprising:

a blade seat configured to receive the blade, the blade seat provided in a first plane;

a handle receptacle configured to receive the handle, the handle receptacle provided in a second plane parallel to said first plane; and;

a generally wedge-shaped member having a sharp upper curved edge existing at least partially in a third plane between and parallel to said first and second planes and at least partially in a plane transverse to said third plane, and also having a sidewall extending away from said upper curved edge towards said handle receptacle;

wherein upon receipt of said blade in said blade seat and said handle in said handle receptacle, movement of said handle away from said transverse plane causes said upper curved edge to be interposed between said blade and said handle and said sidewall to force said blade from engagement with said handle;

wherein the blade seat has an end wall for restraining the blade from rearward movement once the blade has been positioned in the blade seat and the handle withdrawn rearwardly away from the handle receptacle; and a case for housing the blade seat, handle receptacle and generally wedge-shaped member.

2. Apparatus as recited in claim 1, wherein the blade seat, handle receptacle and generally wedge-shaped member are formed of a unitary structure.

3. Apparatus as recited in claim 2, further comprising a magnet disposed within the case for magnetically attracting blades removed from the surgical knife handle.

4. The device of claim 1, wherein the blade receptacle is bordered by the generally wedge-shaped member and the end wall.

5. The device of claim 1, wherein the generally wedge-shaped member remains stationary relative to the blade seat and handle receptacle.

6. A surgical blade removal device for removing a blade from a surgical knife handle, the device comprising:

a blade seat configured to receive the blade, the blade seat provided in a first plane;

a handle receptacle configured to receive the handle, the handle receptacle provided in a second plane parallel to the first plane; and a generally wedge-shaped member having a sharp upper curved edge existing at least partially in a third plane between and parallel to the first and second planes and at least paritally in a plane transverse to said third plane, and also having a sidewall extending away from said upper curved edge towards said handle receptacle;

wherein upon receipt of the blade in said blade seat and the handle in said handle receptacle, movement of said handle away from said transverse plane causes said upper curved edge to be interposed between said blade and said handle and said sidewall to force said blade from engagement with said handle.

7. The device of claim 6, wherein the blade seat has an end wall for restraining the blade from rearward movement once the blade has been positioned in the blade seat and the handle withdrawn rearwardly away from the handle receptacle and wherein the blade receptacle is bordered by the generally wedge-shaped member and the end wall.

8. The device of claim 6, wherein the generally wedge-shaped member remains stationary relative to the blade seat and handle receptacle.

* * * * *